(12) United States Patent
Stalker et al.

(10) Patent No.: US 8,781,208 B2
(45) Date of Patent: Jul. 15, 2014

(54) INSPECTION METHOD AND INSPECTION APPARATUS

(75) Inventors: Marc Philip Stalker, Leyland (GB); Stevan Clee, Wolverhampton (GB)

(73) Assignee: Wilcox Associates, Inc., Telford (GB)

( * ) Notice: Subject to any disclaimer, the term of this patent is extended or adjusted under 35 U.S.C. 154(b) by 12 days.

(21) Appl. No.: 13/318,106

(22) PCT Filed: Apr. 29, 2010

(86) PCT No.: PCT/EP2010/055859
§ 371 (c)(1),
(2), (4) Date: Dec. 5, 2011

(87) PCT Pub. No.: WO2010/145881
PCT Pub. Date: Dec. 23, 2010

(65) Prior Publication Data
US 2012/0070063 A1    Mar. 22, 2012

(30) Foreign Application Priority Data
Apr. 30, 2009    (AU) ................................. 2009901899

(51) Int. Cl.
*G06K 9/00*    (2006.01)
(52) U.S. Cl.
USPC ............ 382/141; 382/145; 382/151; 382/152
(58) Field of Classification Search
None
See application file for complete search history.

(56) References Cited

U.S. PATENT DOCUMENTS

| | | | |
|---|---|---|---|
| 5,333,208 A * | 7/1994 | Massen | 382/111 |
| 5,495,535 A * | 2/1996 | Smilansky et al. | 382/145 |
| 5,699,447 A * | 12/1997 | Alumot et al. | 382/145 |
| 5,982,921 A * | 11/1999 | Alumot et al. | 382/145 |
| 6,175,644 B1 | 1/2001 | Scola et al. | |
| 6,178,257 B1 * | 1/2001 | Alumot et al. | 382/145 |
| 6,397,165 B1 | 5/2002 | Fiekowski | |
| 6,697,517 B1 | 2/2004 | Hunter | |
| 7,027,143 B1 | 4/2006 | Stokowski et al. | |
| 2003/0118230 A1 * | 6/2003 | Song et al. | 382/152 |
| 2003/0206650 A1 * | 11/2003 | Gladnick | 382/141 |
| 2004/0057611 A1 * | 3/2004 | Lee et al. | 382/145 |
| 2004/0217288 A1 * | 11/2004 | Sasajima et al. | 250/310 |
| 2004/0223053 A1 | 11/2004 | Gladnick et al. | |
| 2004/0228515 A1 * | 11/2004 | Okabe et al. | 382/145 |
| 2005/0001900 A1 | 1/2005 | Kreh et al. | |
| 2005/0031191 A1 * | 2/2005 | Venkatachalam | 382/152 |
| 2005/0105792 A1 * | 5/2005 | Cao et al. | 382/145 |
| 2005/0175233 A1 * | 8/2005 | Yoneyama et al. | 382/145 |
| 2005/0275834 A1 * | 12/2005 | Silver | 356/237.1 |
| 2006/0093205 A1 * | 5/2006 | Bryll et al. | 382/152 |
| 2006/0242619 A1 * | 10/2006 | Pang et al. | 716/19 |

(Continued)

FOREIGN PATENT DOCUMENTS

WO    2005100961 A2    10/2005

*Primary Examiner* — Stephen R Koziol
*Assistant Examiner* — Jonathan S Lee
(74) *Attorney, Agent, or Firm* — Maschoff Brennan

(57) ABSTRACT

The application relates to a method of inspecting an object and an inspection apparatus. The object has a plurality of features and the method includes the step of identifying a current primary feature on the object. Once the current primary feature has been selected, one or more additional features are selected, each of the one or more additional features selected having at least one common attribute with the current primary feature. The method also includes the step of capturing an image of the selected features on an image capture module.

13 Claims, 3 Drawing Sheets

(56) References Cited

U.S. PATENT DOCUMENTS

2008/0069428 A1* 3/2008 Schulkin et al. .............. 382/141
2010/0165095 A1* 7/2010 Nakamura ...................... 348/92
2010/0189339 A1* 7/2010 Amanullah et al. .......... 382/145
2010/0246933 A9* 9/2010 Hiroi et al. .................... 382/145

\* cited by examiner

INSPECTION METHOD AND INSPECTION APPARATUS

FIELD OF THE INVENTION

The present invention relates to an inspection method and an inspection apparatus. In particular, although not exclusively, the invention relates to a method of capturing images in a measuring machine environment to thereby undertake optical quality control of objects under inspection.

BACKGROUND TO THE INVENTION

In applications where parts are required to be manufactured to a high level of precision, for example in the airline and aerospace industries, highly accurate quality control mechanisms must be in place in order to ensure that parts are manufactured to specification without divergence from the design or error. Whilst highly accurate manufacturing machines are used to manufacture parts in these industries, errors may still be present in a particular part.

It is impractical and indeed impossible to visually inspect many of these parts by eye and obtain any degree of confidence that the part has been manufactured exactly to specification.

Video measurement machines are used to inspect manufactured parts. These machines generally have an image capture device, such as a digital camera or the like, and data processing and storage capabilities. The part is placed within the field of view of the image capture device and the design technical specification of a manufactured object, referred to in the art as the parts program, is stored within the storage device of the measuring machine.

The parts program includes a series of features associated with the manufactured object. Each feature in the parts program has a series of attributes associated therewith including the feature's geometric properties and spatial location on the object and illumination, magnification and focus settings to allow the measurement machine to capture a suitable image of the feature.

When the parts program is executed, instructions are provided to the operating program of the measurement machine to control the camera and move the camera relative to the object in order to measure each of the features of the object recorded in the parts program. Typically, measurement machine operating programs move through the features recorded in the parts program sequentially and capture the features on the object independently to determine whether the object has been manufactured in accordance with the design specification without error.

For objects that are large and/or have a large number of physical features requiring inspection and measurement, this process can be time consuming. As the measurement and inspection process is part of the manufacturing process, any reduction in the time required to perform this highly accurate quality assurance will deliver reductions in manufacturing time and hence a benefit to the manufacturer.

In this specification, the terms "comprises", "comprising", "includes", "including" or similar terms are intended to mean a non-exclusive inclusion, such that a method, system or apparatus that comprises a list of elements does not include those elements solely, but may well include other elements not listed.

SUMMARY OF THE INVENTION

In one form, although it need not be the broadest form, the invention resides in a method of inspecting an object, the object having a plurality of features, each of the features having one or more attributes associated therewith, the method including the steps of:

identifying a current primary feature of the object;

selecting one or more additional features, each of the one or more additional features selected having at least one common attribute with the current primary feature; and capturing an image of the selected features on an image capture module.

In a further form, the invention resides in an inspection apparatus comprising:

an image capture module adapted to capture a digital image of at least a portion of an object under inspection;

a data store having stored therein a parts list identifying a set of features on the object under inspection, each feature having one or more attributes associated therewith;

an operating system containing computer readable instructions for:

identifying a current primary feature on the object under inspection;

selecting one or more additional features from the parts list, each of the one or more additional features selected having at least one common attribute with the current primary feature; and capturing an image of the selected features using the image capture module.

Further features of the invention will become apparent from the following detailed description.

BRIEF DESCRIPTION OF THE DRAWINGS

By way of example only, preferred embodiments of the invention will be described more fully hereinafter with reference to the accompanying drawings, wherein.

DETAILED DESCRIPTION OF THE INVENTION

Figure 1:
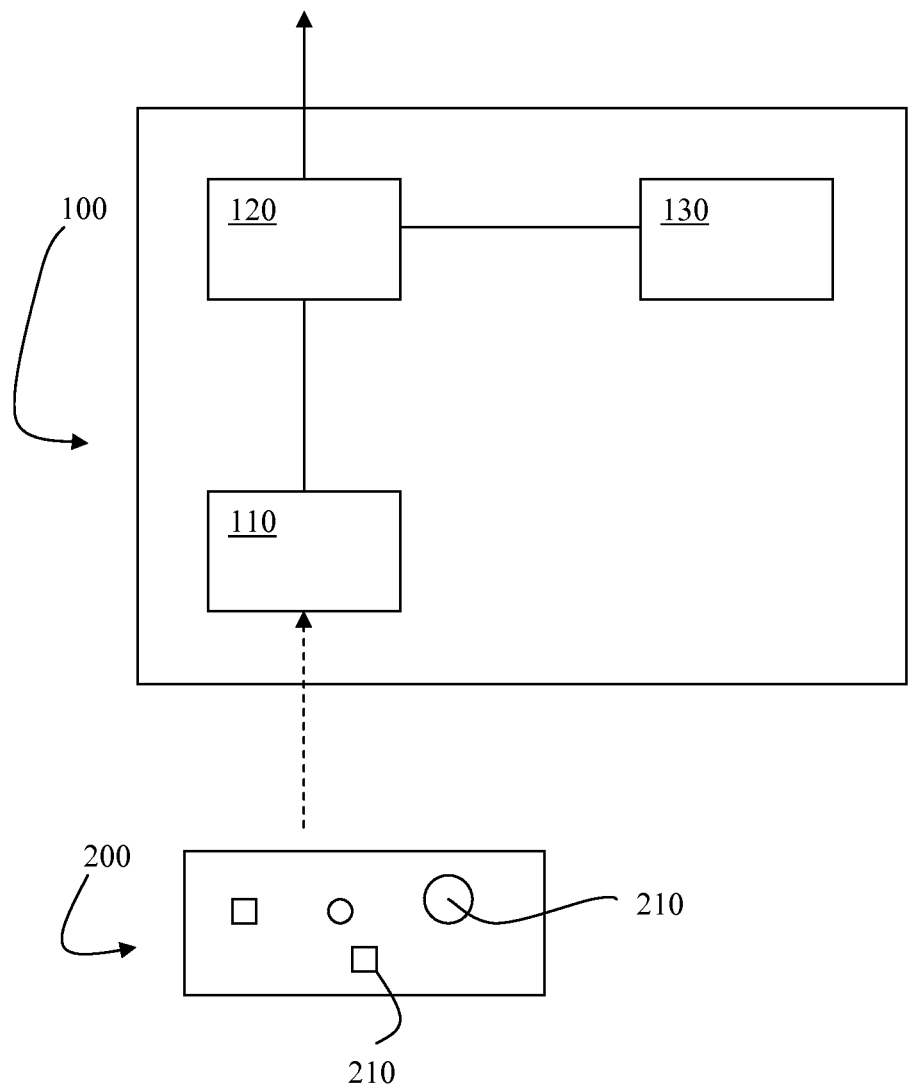
FIG. 1 shows a modular schematic of an inspection apparatus according to an embodiment of the invention.

FIG. 1 shows a schematic view of modules forming part of an inspection apparatus 100 according to an embodiment of the invention. Inspection apparatus 100 comprises an image capture module 110, an operating system 120 and a data storage module 130.

In the embodiment, image capture module 110 is in the form of a digital camera or the like able to capture images of an object under inspection 200. Furthermore, image capture module 110 includes lighting and illumination devices, such as light emitting diodes or the like, to allow appropriate illumination and lighting conditions to allow the digital camera to capture an appropriate image of the object under inspection.

Image capture module 110 is in communication with operating system 120 of inspection apparatus 100 and, in the embodiment, image capture module 110 communicates digital data relating to physical features of the object under inspection 200 to the operating system 120 for processing. Furthermore, operating system 120 communicates with the image capture module 120 to control the focus and magnification characteristics of the digital camera and the illumination levels and color output of the lighting and illumination devices.

Operating system 120 is also in communication with data storage module 130. In the embodiment, data storage module 130 has stored therein a parts program associated with the object under inspection.

The parts program stored within the data storage module 120 contains an identification of the physical features 210 present on the object under inspection 200 together with a series of one or more attributes associated with each feature. These attributes include feature's geometric properties and spatial location on the object and illumination, magnification and focus settings that are required to capture the physical features 210 of the object under inspection 200.

Operating system 120 communicates the result of the inspection of the object to a user of the inspection apparatus 100 as is known in the art.

Figure 2:
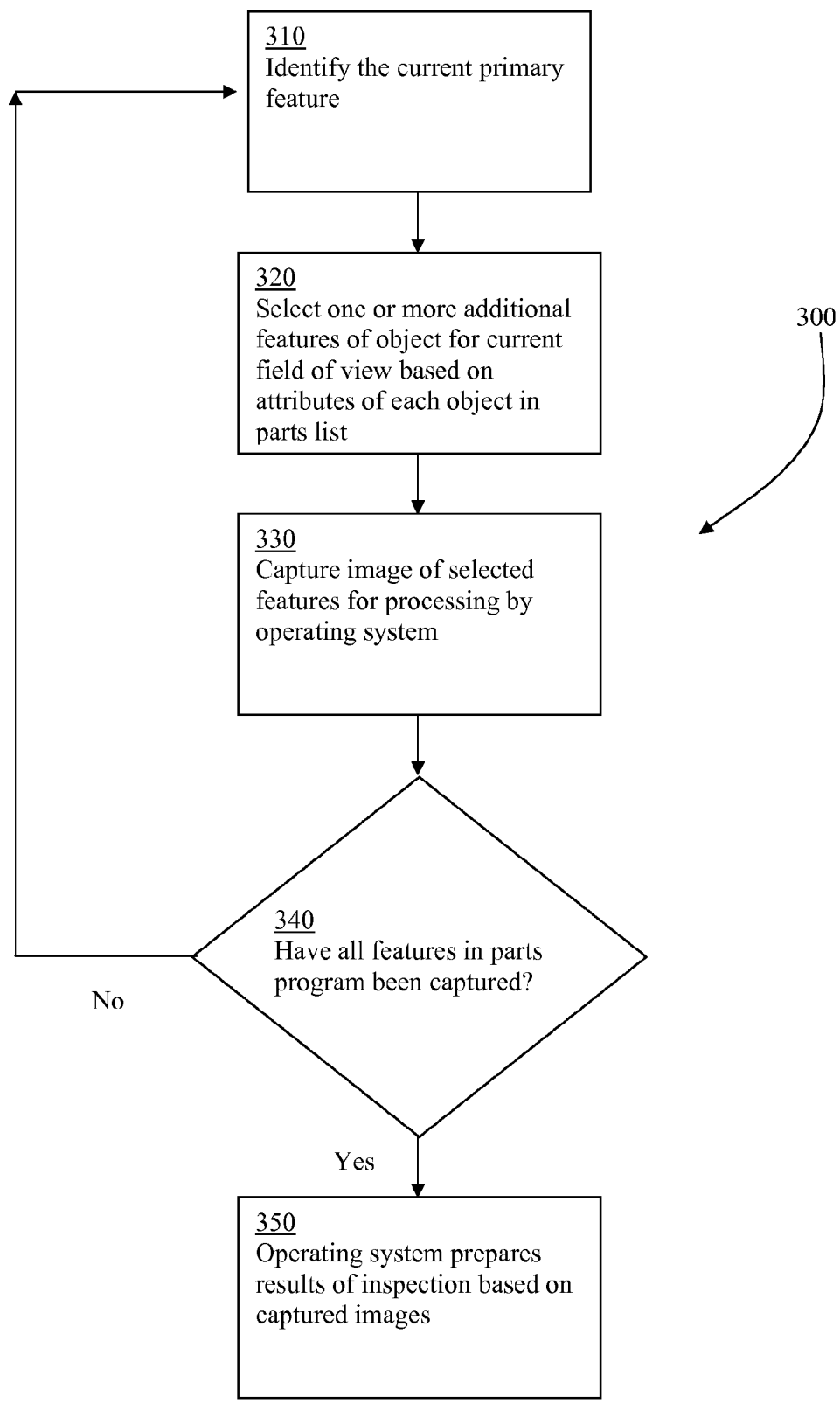
FIG. 2 shows an inspection method according to an embodiment of the invention.

FIG. 2 shows an inspection method 300 according to an embodiment of the invention. The operating system 120 identifies the current primary feature from the features 210 on the object under inspection 200 (step 310). Suitably, the primary feature may be the first feature 210 on the object under inspection 200 in the field of view of the image capture module 110.

Optionally, the primary feature may be the first feature on the parts program stored in the data storage module 130. Alternatively, the primary feature may be the feature in the parts program that is located proximal the centre of the current field of view of the image capture module.

The operating system 120 then selects one or more additional features 210 on the object under inspection 200 based on the attributes associated with each feature 210 located in the parts program stored in the data storage module 120 (step 320) as discussed in greater detail with reference to FIG. 3.

Once the set of selected features has been compiled by the operating system 120, the operating system 120 communicates with the image capture module 110 in order that the image capture module 110 inspects the selected features (step 330). Suitably this occurs by capturing an image of the selected features for processing by the operating system 120 as will be discussed in greater detail below.

The operating system then determines whether all of the features contained in the parts list stored in the data storage module 120 have had their respective features inspected (step 340).

If all features have not been inspected, the operating system 120 then identifies a new primary feature and the method proceeds as previously discussed (step 310).

If all features have been inspected, the operating system prepares the results of the inspection based upon the captured images (step 350). Suitably, this process occurs as is known in the art and the results of the inspection are then communicated for analysis to determine whether the object under inspection 200 has been manufactured to within a desired tolerance.

Figure 3:
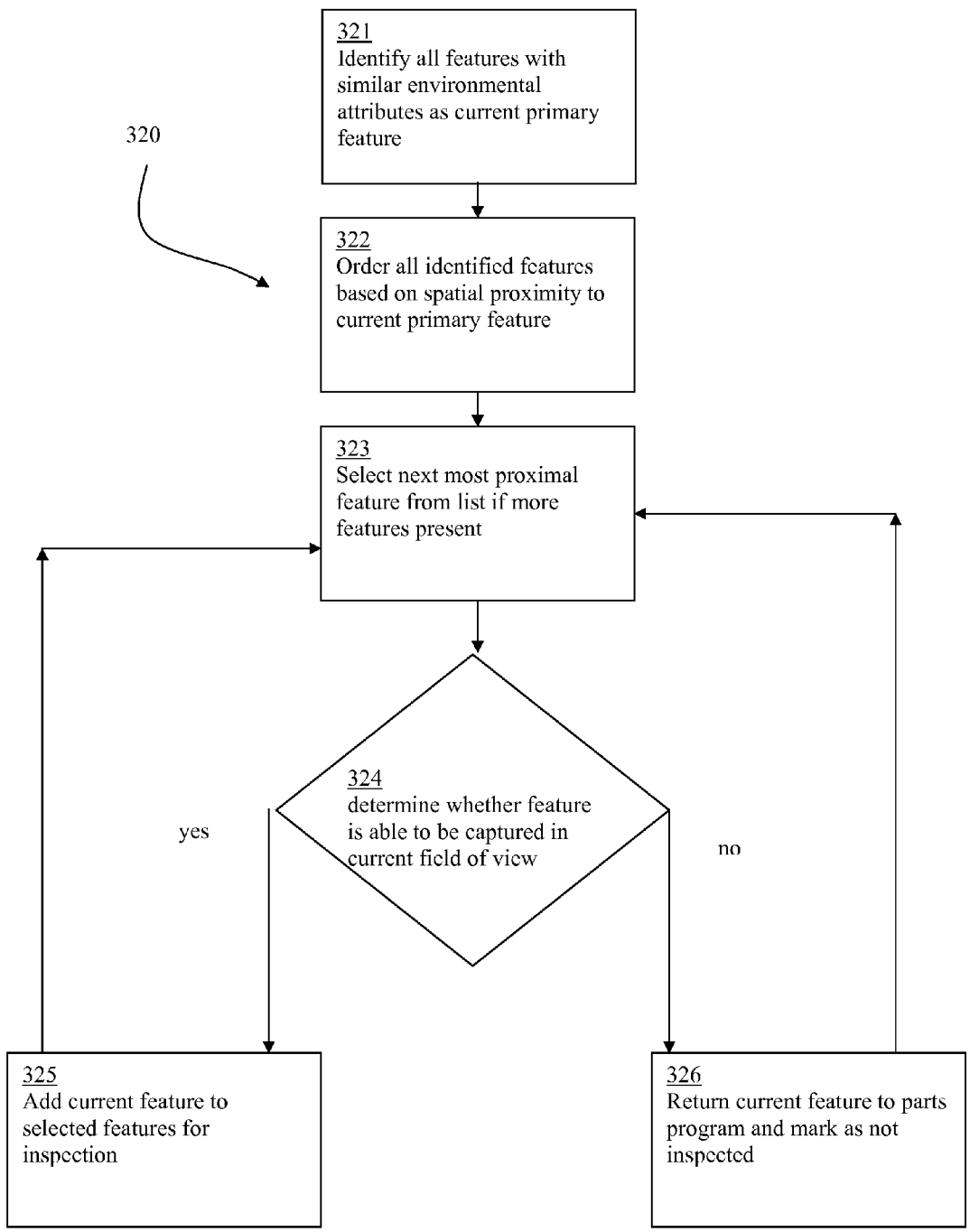
FIG. 3 shows an embodiment of a method of selecting objects forming part of the method shown in FIG. 2.

FIG. 3 shows the step of 320 in greater detail. The operating system 120 parses through the parts program and identifies all features that have identical environmental attributes as the current primary feature (step 321). Suitably, environmental attributes include such attributes as illumination, magnification and focus settings.

The operating system 120 then orders the identified features based on each feature's proximity to the current primary feature (step 322) with the closest feature to the primary feature heading the list. Preferably, the operating system 120 uses the spatial location attribute of each feature during the ordering process.

The operating system 120 then parses the list and selects the next most proximal feature (step 323) and determines whether that feature is able to be captured in the current field of view of the image capture module 110 (step 324). If the list has been exhausted the method continues from step 330 as previously described.

If the next most proximal feature is able to be captured in the current field of view of the image capture module 110, that feature is selected for inspection (step 325).

If the next most proximal feature is not able to be captured in the current field of view of the image capture module 110, that feature is discarded and returned to the parts program for later inspection (step 326).

The method and system of the invention reduces the amount of movement of the image capture device relative to the object and the number of actual image captures is reduced. In this way, time for inspection is minimized which results in subsequent cost savings to the owner.

Throughout the specification the aim has been to describe the present invention without limiting the invention to any one embodiment or specific collection of features. Persons skilled in the relevant art may realize variations from the specific embodiments that will nonetheless fall within the scope of the present invention.

The invention claimed is:

1. A method of inspecting an object, the object having a plurality of physical features, each of the features having one or more attributes associated therewith, the attributes comprising:
   geometric properties of the feature;
   spatial location of the feature on the object; or
   environmental attributes,
the method including the steps of:
   identifying a current primary feature of the object;
   selecting one or more additional features, each of the one or more additional features selected having at least one common attribute with the current primary feature;
   capturing an image of the selected features on an image capture module;
   determining, in an operating system of an inspection apparatus, whether the selected features of the captured image have been manufactured to within a predetermined tolerance; and
   communicating whether the selected features have been manufactured to within a predetermined tolerance,
   wherein the step of identifying a current primary feature of the object involves selecting:
      a first feature on a parts list stored in a data store;
      a first feature in a current field of view of the image capture module; or
      a feature located proximal the center in a current field of view of the image capture module; and
   wherein selecting one or more additional features involves the steps of:
   identifying all features on the object that have environmental attributes identical to the environmental attributes of the current primary feature;
   determining whether each of the identified features is able to be captured in a current field of view of the image capture module, involving parsing, in an operating system of an inspection apparatus, an ordered list of the identified features, whereby the ordered list is ordered on the basis of each feature's proximity to the current primary feature; and
   selecting an identified feature if the identified feature is within the current field of view of the image capture module.

2. The method of claim 1, wherein each feature and each of the one or more attributes associated with each feature are stored in a parts list in a data store of an inspection apparatus.

3. The method of claim 1, wherein an identified feature is returned to a parts list in a data store of an inspection apparatus and has associated therewith an indication that the identified feature has not been selected if the identified feature is not within the current field of view of the image capture module.

4. The method of claim 1, wherein environmental attributes include illumination settings of the image capture module, magnification settings of the image capture module and focus settings of the image capture module.

5. An inspection apparatus comprising:
an image capture module adapted to capture a digital image of at least a portion of an object under inspection; and
a data store having stored therein a parts list identifying a set of physical features on the object under inspection, each feature having one or more attributes associated therewith each attribute comprising at least geometric properties of the feature, spatial location of the feature on the object or environmental attributes;
an operating system containing computer readable instructions for:
identifying a current primary feature on the object under inspection;
selecting one or more additional features from the parts list, each of the one or more additional features selected having at least one common attribute with the current primary feature; and
capturing an image of the selected features using the image capture module;
determining whether the selected features of the captured image have been manufactured to within a predetermined tolerance; and
communicating whether the selected features have been manufactured to within a predetermined tolerance,
wherein identifying a current primary feature of the object involves selecting:
a first feature on the parts list stored in the data store;
a first feature in a current field of view of the image capture module; or
a feature located proximal the center in a current field of view of the image capture module; and
wherein selecting one or more additional features involves the steps of:
identifying all features on the object that have environmental attributes identical to the environmental attributes of the current primary feature;
determining whether each of the identified features is able to be captured in a current field of view of the image capture module, involving parsing, in an operating system of an inspection apparatus, an ordered list of the identified features, whereby the ordered list is ordered on the basis of each feature's proximity to the current primary feature; and
selecting an identified feature if the identified feature is within the current field of view of the image capture module.

6. The inspection apparatus of claim 5, wherein the image capture module is a digital camera operable under instruction from the operating system.

7. The inspection apparatus of claim 5, wherein the environmental attributes include illumination settings of the image capture module, magnification settings of the image capture module and focus settings of the image capture module.

8. The inspection apparatus of claim 6, wherein the environmental attributes include illumination settings of the image capture module, magnification settings of the image capture module and focus settings of the image capture module.

9. The method of claim 3, wherein environmental attributes include illumination settings of the image capture module, magnification settings of the image capture module and focus settings of the image capture module.

10. The method of claim 3, wherein the step of determining whether each of the identified features is able to be captured in a current field of view of the image capture module involves parsing, in an operating system of an inspection apparatus, an ordered list of the identified features, whereby the ordered list is ordered on the basis of each feature's proximity to the current primary feature.

11. The method of claim 4, wherein the step of determining whether each of the identified features is able to be captured in a current field of view of the image capture module involves parsing, in an operating system of an inspection apparatus, an ordered list of the identified features, whereby the ordered list is ordered on the basis of each feature's proximity to the current primary feature.

12. The method of claim 1, wherein the communicating is the operating system communicating to a user of the inspection apparatus.

13. The inspection apparatus of claim 5, the operating system containing computer readable instructions for the operating system communicating whether the selected features have been manufactured to within a predetermined tolerance to a user of the inspection apparatus.

* * * * *